(12) United States Patent
Saito et al.

(10) Patent No.: US 7,465,470 B2
(45) Date of Patent: Dec. 16, 2008

(54) PROCESS FOR PRODUCING A SOYBEAN PROTEIN USABLE IN ACIDIC FOODS

(75) Inventors: Tsutomo Saito, Tsukuba-gun (JP); Keisuke Tsuge, Saga (JP); Toshio Kiriyama, Tsukuba-gun (JP); Wataru Kugimiya, Tsukuba-gun (JP)

(73) Assignee: Fuji Oil Company, Limited, Osaka (JP)

( * ) Notice: Subject to any disclaimer, the term of this patent is extended or adjusted under 35 U.S.C. 154(b) by 525 days.

(21) Appl. No.: 10/469,348

(22) PCT Filed: Feb. 25, 2002

(86) PCT No.: PCT/JP02/01678

§ 371 (c)(1),
(2), (4) Date: Aug. 28, 2003

(87) PCT Pub. No.: WO02/067690

PCT Pub. Date: Sep. 6, 2002

(65) Prior Publication Data

US 2004/0086624 A1 May 6, 2004

(30) Foreign Application Priority Data

Feb. 28, 2001 (JP) .................. 2001-0153478

(51) Int. Cl.
 *A23L 1/20* (2006.01)
(52) U.S. Cl. .................... 426/656; 426/634
(58) Field of Classification Search .......... 426/656, 426/634
See application file for complete search history.

(56) References Cited

U.S. PATENT DOCUMENTS

| | | | |
|---|---|---|---|
| 3,736,147 A * | 5/1973 | Iacobucci et al. ........ 530/377 |
| 3,852,503 A | 12/1974 | Magnino et al. | |
| 3,853,839 A | 12/1974 | Magnino et al. | |
| 3,966,971 A | 6/1976 | Morehouse et al. | |
| 4,062,987 A * | 12/1977 | Hildebolt ............ 426/641 |
| 4,088,795 A * | 5/1978 | Goodnight et al. ...... 426/598 |
| 4,697,004 A * | 9/1987 | Puski et al. ............ 530/378 |
| 5,658,714 A * | 8/1997 | Westfall et al. ......... 530/378 |
| 6,071,547 A * | 6/2000 | Schechter ............. 426/590 |
| 6,638,562 B1 | 10/2003 | Saitoh et al. | |
| 2001/0018197 A1 * | 8/2001 | Wong et al. .......... 435/68.1 |

FOREIGN PATENT DOCUMENTS

| | | |
|---|---|---|
| JP | 48-18450 | 3/1973 |
| JP | 48-80754 | 10/1973 |
| JP | 51-125300 | 11/1976 |
| JP | 53-19669 | 6/1978 |
| JP | 62-143653 * | 6/1987 |
| JP | 63-169939 | 7/1988 |
| JP | 2-265440 | 10/1990 |
| JP | 4-311354 | 11/1992 |
| JP | 6-86640 | 3/1994 |
| JP | 2000-83595 | 3/2000 |
| WO | 00/58492 | 10/2000 |
| WO | 00/62623 | 10/2000 |

OTHER PUBLICATIONS

Office Action in corresponding Chinese Patent Application No. 02805680.9, Feb. 25, 2002, with English translation.
C.A. Prattley et al., "Protein-Phytate Interactions in Soy Beans. II. Mechanism of Protein-Phytate Binding as Affected by Calcium", Journal of Food Biochemistry, vol. 6, pp. 255-271, 1982.

* cited by examiner

*Primary Examiner*—Anthony Weier
(74) *Attorney, Agent, or Firm*—Wenderoth, Lind & Ponack, L.L.P.

(57) ABSTRACT

It is intended to provide a soybean protein material which is excellent in solubility, stability, emulsifying properties and gel-forming properties under acidic conditions and thus advantageously usable in acidic foods, its production process, and acidic foods using the soybean protein material. A solution containing soybean protein is subjected to a treatment for eliminating or inactivating polyanionic substances contained therein and/or adding a polycationic substance and then heated at above 100° C. under acidic conditions. Thus, a soybean protein having a high solubility under acidic conditions and thus being appropriately usable in acidic foods can be obtained. By using this protein, protein foods in an acidic region can be provided. Further, by combining the above-described treatment with a protease-digestion treatment, a soybean protein hydrolysate having a high solubility in an acidic region can be efficiently obtained.

8 Claims, No Drawings

PROCESS FOR PRODUCING A SOYBEAN
PROTEIN USABLE IN ACIDIC FOODS

TECHNICAL FIELD

The present invention relates to a soybean protein material which exhibits good solubility in an acidic region and can be advantageously used in acidic foods, and its production process as well as a protein food using the material and its production process.

BACKGROUND ART

Soy bean proteins have been utilized as an excellent edible protein source for a long time. In addition, since they have various functional properties such as emulsifying and gel-forming capabilities, they have been widely used as a raw material for foods or a material for improving quality of foods in edible meat products, fishery paste products, side dishes, bread, confectionery and a raw material for beverages. Further, recently, it has been elucidated that soybean proteins reduce blood cholesterol level and their nutritional and physiological functions have been noted.

On the other hand, in so-called acidic foods having pH below 4.6 (Ed. by Isao SHIBASAKI, "Sakkin and/or Jokin Ohyo Handbook (Sterilization and/or Disinfection Application Handbook)", SCIENCE FORUM, p. 28), the use of soybean proteins is restricted because soybean proteins scarcely dissolve and do not exhibit their functional properties in a pH region where they are frequently used (pH 3.0 to 4.5). This is due to pH of acidic foods which is equal to or in the vicinity of the isoelectric point of a soybean protein (about pH 5).

Many techniques in the prior art relating to utilization of soybean proteins in acidic foods are mainly directed to prevention of aggregation and/or precipitation of soybean proteins in an acid region in the production of acidic beverages. For example, there have been known the addition of stabilizers such as pectin (JP 54-52754 A), and emulsifiers such as a sugar fatty acid ester having HLB of 13 or more (JP 59-41709 B).

The following will illustrate the conditions of a protein at the time of addition of a stabilizer. In a solution containing a soybean protein which is adjusted to pH 3.0 to 4.5, the protein in the system has a positive surface charge, but an absolute value of the charged amount is low because pH is in the vicinity of the isoelectric point. Then, the protein is liable to form aggregation and/or precipitation. A stabilizer, whose typical examples include polyanionic polysaccharides such as pectin, propylene glycol alginate, carboxymethylcellulose, etc., interacts with a protein having a positive charge and a stabilizer molecule adheres thereto to form protein granules each of which as a whole has a negative surface charge, thereby avoiding aggregation and/or precipitation owing to electric repulsion between the granules. However, these techniques using stabilizers or emulsifiers are not those for obtaining a dissolution state of a protein itself but those to be applied and utilized at the time of formulating a protein material and other materials. Then, a product having a transparent appearance can not be obtained and functional properties of a protein material itself such as emulsifying and gel-forming capabilities are hardly expected.

On the other hand, methods for suppressing aggregation due to passing the isoelectric point of a soybean protein have also been proposed (JP 7-16084 A and JP 12-77 A). However, since the addition of a stabilizer or emulsifier is required, the conditions of a protein are the same as those described above.

As a method for increasing solubility of a protein in an acidic region of below its isoelectric point, for a soybean protein, there is a method disclosed in JP 53-19669 B. In this method, a slurry of a soybean protein isolate having a solid content of 10 to 15% by weight is prepared at pH about 2.0 to about 4.2 and the slurry is subjected to a heat treatment at a temperature of about 120 to 160° C. by a continuous process.

However, a problem in solubility of a soybean protein in an acidic region still remains in this method. When a soybean protein slurry is adjusted to pH 3.0 to 3.5 and subjected to a heat treatment at a high temperature, the protein molecule forms a dispersed state, but it is a cloudy solution. Further, precipitation of the protein is caused during storage. This is not suitable for using the protein in protein foods in an acid region, particularly, in acidic protein beverages. Furthermore, a cloudy protein obtained by this method has poor functional properties such as emulsifying and gel-forming capabilities and its utility as a food improving material, which is expected for a normal soybean protein isolate, is remarkably restricted.

In addition, JP 55-29654 B discloses a method for isolating a soluble protein fraction, wherein a fraction soluble at pH below 4.6 can be isolated by combination of a phytase treatment and fractionation by pH adjustment. However, in this method, the product is obtained in low yield such as 14% by using a soybean protein isolate as a starting material. Therefore, this method is less practical.

JP 51-125300 A discloses a process for producing a protein having excellent solubility at pH 3 to 5 by washing defatted soybeans with an acid, treating the soybeans with an acidic phytase derived from a microorganism at pH 2 to 6 and separating a solubilized fraction. However, the protein obtained by this process is highly hydrolyzed by a protease. In addition, both solubilized and insolubilized fractions are formed and their separation is required. Then, the objective soybean protein having high solubility is obtained in low yield.

Thus, a soybean protein material, which can be utilized in an acidic food of pH lower than 4.6 and is soluble in a range of pH 3.0 to 4.5, and whose solution has preferred transparency in appearance and excellent storage stability together with functional properties such as emulsifying and gel-forming capabilities, has not been obtained heretofore in the prior art. Further, no process has been known for producing a soybean protein hydrolysate having high solubility and storage stability in the above pH range, efficiently.

DISCLOSURE OF THE INVENTION

The present invention is to provide a soybean protein, which can be utilized in an acidic food of pH lower than 4.6, is soluble in a range of pH 3.0 to 4.5 and has excellent storage stability and, in particular, whose solution obtained by using a defatted protein source has preferred transparency in appearance and functional properties such as emulsifying and gel-forming capabilities, as well as its production process and an acidic protein food using the soybean protein.

The present inventors have studied intensively for producing a soybean protein which can be widely utilized in an acidic food of pH lower than 4.6 and is soluble in a range of pH 3.0 to 4.5, and whose solution has preferred transparency in appearance and excellent storage stability together with functional properties such as emulsifying and gel-forming capabilities. As a result, it has been found that an original cloudy protein solution can be converted into a solubilized state having transparency by subjecting to the following treatments. The treatments are to subject a solution containing a soybean protein to either or both of (A) a treatment for eliminating or inactivating polyanionic substances which are derived from the protein source and contained in the solution, and (B) a treatment for adding a polycationic substance to the solution, as a treatment for increasing the positive surface charge of soybean protein in the system; and then subjecting the protein solution to a heat treatment at a temperature of above 100° C. in an acidic region of pH below the isoelectric point of the protein. Further, for enhancing handiness in the utilization of this protein, a powdered soybean protein can be obtained by drying the above treated material at pH 4.5 or below.

By the above process, there can be obtained a soybean protein material whose main component is globulin having solubility at pH 4.5 or lower of 90% or more, transmittance at 600 nm (a solution containing 5% by weight of protein) of 20% T or more, and a 0.22M/TCA solubilization degree of 20% or less.

As the treatment for increasing the positive surface charge of soybean protein in the system, in general, there are a treatment for eliminating or inactivating polyanionic substances contained in vegetable proteins such as phytic acid, addition of a polycationic substance, or a combination of these treatments.

That is, according to the present invention, a soybean protein exhibiting excellent solubility and storage stability in an acidic region and having functional properties such as emulsifying and gel-forming capabilities can be obtained by subjecting a solution containing a soybean protein to the above treatments.

Further, according to the present invention, there can be obtain a soybean protein hydrolysate having good solubility without carrying out an operation for removing insoluble matter by subjecting a solution containing a soybean protein to combination of treatments of either or both of a treatment for eliminating or inactivating substances, and a treatment for adding a polycationic substance to the solution, as the treatment for increasing the positive surface charge of protein in the system; and hydrolyzation of the protein with a protease; followed by subjecting the protein solution to a heat treatment at a temperature of above 100° C. in an acidic region of pH below the isoelectric point of the protein, specifically pH 4.3 or lower.

Basically, in the treatments of the process of the present invention, there is no loss of a protein toward the outside of system and there is no loss in yield.

BEST MODE FOR CARRYING OUT THE INVENTION

Hereinafter, preferred embodiments of the present invention will be described. The solution containing soybean protein used in the present invention corresponds to soybean milk made from soybeans, extracts obtained by removing insoluble fibrous components (okara) from defatted soybeans, and the like. In the present invention, a solution of a protein component from which a fat component has been removed is particularly preferred for obtaining a soybean protein having high transparency. Further, a solution of a soybean protein hydrolyzed by a protease is also preferred.

<Solubility, Transmittance, TCA Solubilization Degree>

The solubility (%) used in the present invention is a measure of solubilization of a protein in a solvent and is defined as follows. That is, a solution is prepared by dispersing a protein powder in water so that the protein content is 5.0% by weight and thoroughly stirring the resultant dispersion to obtain a solution. After adjusting pH if necessary, the solution is centrifuged at 10,000 G for 5 minutes, and the ratio of a protein in the resultant supernatant to the total protein is determined by a protein determination method such as Kjeldahl method, Lowry's method, and the like to obtain the solubility.

The transmittance (% T) used in the present invention is a measure of transparency of a solution containing a protein and is defined as follows. That is, a solution is prepared by dispersing a protein powder in water so that the protein content is 5.0% by weight and thoroughly stirring the resultant dispersion to obtain a solution. After adjusting pH if necessary, the transmittance (% T) at 600 nm is measured with a spectrophotometer (U-3210 autographic spectrophotometer manufacture by Hitachi) using a 1 cm cell.

The TCA solubilization degree (%) used in the present invention is a measure of a degradation degree of a protein and is defined as follows. That is, a solution is prepared by dispersing a protein powder in water so that the protein content is 1.0% by weight and the resultant dispersion is thoroughly stirred to obtain a solution. Then, the ratio of a 0.22 M trichloroacetic acid (TCA)-solubilized protein in the solution to the total protein is determined by a protein determination method such as Kjeldahl method, Lowry's method, and the like to obtain the TCA solubilization degree.

<Treatment for Increasing Positive Surface Charge>

The following will illustrate the treatment for increasing the positive surface charge of protein in the system to be carried out in the solution containing protein which has been adjusted below the isoelectric point according to the present invention. In other words, the increase in the positive surface charge in the system can be realized by eliminating or inactivating polyanionic substances present in the system, or by adding a polycationic substance to the system. In case of a soybean protein, it contains phytic acid as a polyanionic substance. Therefore, it is important to eliminate or inactivate phytic acid.

In any treatments, the protein can be recovered with no loss thereof toward the outside of system.

<Phytase Treatment>

In the present invention, a treatment for reducing phytin is suitable for eliminating polyanionic substances in the solution containing soybean protein. This treatment for reducing phytin is not limited to a specific method and a known method can be utilized. Examples thereof include treatments with membrane such as dialysis, ultrafiltration, and electrodialysis, treatments with an ion exchange resin, and the like. As the desired and practical treatment for reducing phytin, there is a method using an enzyme or enzyme preparation having a phytic acid-hydrolyzing activity (phytase).

In case that hydrolysis of a protein is undesirable, preferably, the phytase to be used in the present invention should have a low or no protease activity. When the protease activity is high, a protein is hydrolyzed by the protease, which causes problems, for example, lowering of functional properties such as gel-forming capability, deterioration of taste due to an increase in low molecular hydrolysates, and the like. For example, the conditions of no or less hydrolysis of a protein by a protease can be defined by the TCA solubilization degree of a protein of 20% or less, preferably, 15% or less after treatment with a phytic acid-hydrolyzing enzyme. Although the origin of the enzyme or enzyme preparation is not specifically limited in so far as the enzyme or enzyme preparation has a phytic acid-hydrolyzing activity which meets the above-described conditions, in general, a phytase derived from a microorganism is more advantageous than that derived from a plant in view of prevention of hydrolysis and spoilage of a protein because the former has a higher phytic acid-hydrolyzing activity and a lower coexisting protease activity.

In the present invention, the reduction of phytic acid contributes to improvement of solubilization and, the more phytic acid is reduced, the more solubilization is improved. It is desirable to reduce the amount of phytic acid to 1% by weight or less based on the weight of a protein. For example, usually, a curd slurry prepared by extracting defatted soybeans with water, removing okara from the extract and subjecting the resultant extract to acid precipitation contains about 2% by weight of phytic acid based on the weight of a protein. Then, in this case, it is preferred to hydrolyze phytic acid so that the phytic acid content becomes about 50% or less of that before the reaction. Conditions of the phytase treatment is not specifically limited and a method for reacting a phytase is not limited, either, in so far as the above conditions are met, because a phytase can be reacted under optimum conditions. For example, such conditions include a reaction at pH 2.5 to 7.5 and a temperature of 20 to 70° C., with a phytase in an amount of 0.1 to 100 units/g, preferably 0.5 to 50 units/g of the solid content, normally for 5 minutes to 3 hours. However, when denaturation and spoilage of a protein can be avoided, there is no difficulty in carrying out the reaction under conditions outside of the above range. When the treatment should be carried out within a shorter period of time, higher units of the enzyme may be used in the reaction. One unit of a phytase activity represents the amount of an enzyme required for releasing 1 μmol of phosphoric acid from the substrate, phytic acid, during one minute of the initial stage of the reaction under standard conditions (pH 5.5, 37° C.). The degree of hydrolysis of phytic acid and its salt was determined by directly measuring the phytic acid content in a solution according to a method of Alii Mohamed (Cereal Chemistry, 63, 475, 1986).

<Addition of Metal Ion>

Inactivation of polyanionic substances means to inhibit the attachment of a polyanion such as phytic acid to a soybean protein and can be carried out by addition of a polyvalent metal ion of divalent or higher. The polyvalent metal ion of divalent or higher to be added to the solution containing soybean protein in the present invention is a water-soluble salt or a hydroxide of a metal such as calcium, magnesium, iron, zinc, aluminum, or the like, and either of inorganic and organic salts can be used. These metal ions can be used alone or as a mixture thereof. Although the improving effect of solubility and transparency of a soybean protein after the heat treatment at a temperature above 100° C. can be obtained by the addition of these metal ions alone, such effect can be significantly enhanced by combining with the treatment for eliminating polyanionic substances such as the treatment for reducing phytin, or the like. The more the amount of a polyvalent metal ion of divalent or higher is, the more solubilization is improved. However, the preferred amount is 0.2 to 3% by weight in terms of a metal ion based on the solid content in the solution containing protein. When the amount is less than this range, solubilization of the protein is insufficient and, when the amount is more than this range, thickening or aggregation tends to be caused. This is undesirable. A method of addition is not specifically limited.

<Addition of Polycationic Substance>

As the polycationic substance to be added to the solution containing soybean protein in the present invention, chitosan is exemplified. Chitosan is a deacetylation product of chitin and a polymer of glucosamine. In general, chitosan is produced from shells come from the processing of crustaceans such as lobsters, crabs, and the like. In the present invention, chitosan to be added to the solution of soybean protein is preferably water-soluble and that having, for example, a deacetylation degree of 50% or more, preferably, 70% or more is used. Although the improving effect of solubility and transparency of a soybean protein after the heat treatment at a temperature above 100° C. can be obtained by the addition of chitosan alone, such effect can be significantly enhanced by combining with the treatment for eliminating or inactivating polyanionic substances. The amount of chitosan to be added is 0.2% by weight or more based on the solid content of the solution containing soybean protein. When the amount is less than this range, solubilization of the protein is insufficient. Although solubilization is improved as increase in the amount to be added, sometimes, there are such disadvantages that thickening is caused depending on a kind of chitosan, and peculiar bitterness of chitosan becomes strong. Although the amount of chitosan to be added can not be evenly defined, the amount is preferably 40% by weight or less based on the solid content of the solution. Since, in case of chitosan, solubility varies depending on pH of a solvent, it is desirable to add chitosan to the solution containing soybean protein in an acidic region (e.g., pH 5.0 or lower).

<Heating, Drying Treatment>

The solution containing soybean protein, which has been subjected to the treatment for reducing phytin to reduce the phytic acid content to 1% by weight or less based on the weight of the protein, to which a polyvalent metal ion of divalent or higher has been added or a polycationic substance has been added, or which have been subjected to a combination of the above treatments, is adjusted to the solid content of 3 to 18% by weight, preferably 8 to 14% by weight and pH 2.3 to 4.3. Then, the solution is heated at 100 to 160° C., preferably 105 to 145° C. In case of pH lower than 2.3, while a protein solution having high transparency can be obtained, an amount of an acid used is remarkably increased and this is undesirable in view of taste of the protein and practical value. In case of pH higher than 4.3, this is undesirable because the solution tends to be cloudy and liable to form aggregation.

In case of the solid content of 3% by weight or lower, although there is no problem in quality, operation efficiency is bad. This is undesirable. In case of the solid content of 18% by weight or higher, viscosity of the protein solution is remarkably increased and, sometimes, workability in subsequent steps is deteriorated. This is undesirable. However, when the soybean protein is a hydrolysate, increase in viscosity does not influence so much, and its concentration may be increased.

In case of a heating temperature of 100° C. or lower, solubilization of the protein is insufficient and a level of transparency is low. In case of a temperature of higher than 160° C., functions and nutrition of the protein is likely to be deteriorated due to cleavage of peptide bonds, etc., and this is undesirable. The heating time is not specifically limited and may be several seconds to 60 minutes, while it should be noted that heating for a too long period of time adversely influences quality such as taste, and the like. Any heating system can be employed and, for example, a continuous direct heat sterilization apparatus having a steam injection system is preferred. This apparatus can raise a temperature to above 100° C. momentarily by blowing steam into a liquid flowing through a tube in the apparatus. The solution containing soybean protein after heating can be used in the form of a solution as it is or, in order to enhance handiness for utilization, it can be powdered. In this case, preferably, the solution obtained is dried at pH 4.5 or lower to obtain a powder. When the drying is carried out at pH higher than 4.5, solubility of the resultant powder in an acidic region is lowered. This is undesirable.

A drying method is not specifically limited and a spray drying apparatus, etc., are suitable. The soybean protein obtained by the present invention is solubilized even at pH 3.5 to 4.5 where solubility of a common protein is low. Particularly, the solution having high transparency can be obtained from a defatted raw material.

<Hydrolysis>

As for the hydrolysis by a protease of the present invention, it is sufficient to carry out the hydrolysis prior to subjecting the protein solution to the step for the heat treatment at a temperature above 100° C. in an acidic region of pH below the isoelectric point of the protein, and can be carried out prior to, after or at the same time of subjecting the solution containing soybean protein to the treatment for eliminating or inactivating polyanionic substances, or the treatment for adding a polycationic substance to the solution. The protease to be used, conditions of hydrolysis of the protein, the amount of the protease to be added are not specifically limited.

<Foods Utilizing Soybean Protein>

Usually, it is very difficult to obtain a protein food having transparency in an acidic region such as in vicinity of the isoelectric point because of aggregation of the protein. A protein beverage having transparency in an acidic region and good storage stability without precipitation of a protein can be produced by using the soybean protein material or the hydrolysate of soybean protein of the present invention. When a protein beverage is produced, the product can be flavored by selecting saccharides, flavors, etc., according to consumers' tastes. The content of the protein depends on the necessity of intake of the protein, but preferably within the range of several to several tens percents. Further, an acidic jelly food having transparency can be produced by using the soybean protein material or the hydrolysate of soybean protein of the present invention together with an appropriate gel-forming agent.

EXAMPLES

Hereinafter, the present invention will be specifically illustrated by Examples. It should be noted that they are mere exemplification and the technical scope of the present invention is not limited thereto.

Example 1

Preparation: Phytase Treatment

Soybeans were pressed into flakes and the oil is extracted, separated and removed by using n-hexane as an extraction solvent to obtain defatted soybeans with less denaturation (nitrogen soluble index (NSI): 91). To 1 part by weight of the soybeans was added 7 parts of water and the mixture was adjusted to pH 7 with a diluted sodium hydroxide solution and extracted with stirring at room temperature for 1 hour. The mixture was centrifuged at 4,000 G, and okara and insoluble matter were separated to obtain defatted soybean milk. The defatted soybean milk was adjusted to pH 4.5 with phosphoric acid and centrifuged at 2,000 G with a continuous centrifugal separator (decanter) to obtain an insoluble fraction (acid precipitated curd) and a soluble fraction (whey). Water was added to the acid precipitated curd so that the solid content was 10% by weight to obtain an acid precipitated curd slurry. This was adjusted to pH 3.5 with phosphoric acid and then warmed to about 40° C. To the resultant solution (phytic acid content: 1.96% by weight/solid content; TCA solubilization degree: 4.6%) was added a phytase ("Sumityme PHY" manufactured by Shin Nippon Kagaku Kogyo) in an amount corresponding to 8 units relative to the solid content and the enzymatic reaction was carried out for 30 minutes. After completion of the reaction, the reaction mixture thus treated with the enzyme (phytic acid content: 0.04% by weight/solid content; TCA solubilization degree: 4.7%) was adjusted to pH 3.0, 3.5, or 4.0 with phosphoric acid or sodium hydroxide. Each of them was heated with a continuous direct heat sterilization apparatus at 120° C. for 15 seconds. Each of the resultants was spray-dried to obtain a soybean protein powder.

When the globulin content of the soybean protein powder obtained in this Example by treating at pH 3.5 was determined by ELISA method with SOYA PROTEIN ASSY KIT (manufactured by Tepnel Bio Systems, Ltd.), it was 74.0% by weight based on the solid content. This showed that the main component of this protein was globulin.

Comparative Example 1

Heating Alone

The acid precipitated curd slurry having the solid content of 10% by weight prepared in Example 1 was adjusted to pH 3.0, 3.5 or 4.0 with phosphoric acid. Then, the slurry was heated with a continuous direct heat sterilization apparatus at 120° C. for 15 seconds. Each of the resultants was spray-dried to obtain a soybean protein powder. However, since the solution adjusted to pH 4.0 formed remarkable aggregation during heating, the subsequent spray drying thereof was not carried out.

Example 2

Preparation: Treatment by Addition of Chitosan

The acid precipitated curd slurry having the solid content of 10% by weight prepared in Example 1 was adjusted to pH 3.5 with phosphoric acid. To the slurry was added chitosan (Chitosan LL manufactured by Yaezu Suisan Kagaku Kogyo; deacetylation degree: 80% or higher; 1% viscosity: 10 cps or higher) in an amount of 5.0% by weight based on the solid content. After thoroughly stirring, the resultant solution was heated at pH 3.0 with a continuous direct heat sterilization apparatus at 120° C. for 15 seconds. This was spray-dried to obtain a soybean protein powder.

Example 3

Preparation: Addition of Metal Ion

The acid precipitated curd slurry having the solid content of 10% by weight prepared in Example 1 was adjusted to pH 3.0 with phosphoric acid. Then, to the slurry was added calcium chloride dihydrate (manufactured by Kishida Kagaku) in an amount of 5.0% by weight based on the solid content (1.35% by weight in terms of calcium ion). After thoroughly stirring, the resultant solution was heated at pH 3.5 with a continuous direct heat sterilization apparatus at 120° C. for 15 seconds. This was spray-dried to obtain a soybean protein powder.

Example 4

Preparation: Phytase+Chitosan

To the reaction mixture treated with phytase in Example 1 was added chitosan as described in Example 2 in an amount of 1.0% by weight based on the solid content. After thoroughly stirring, the solution was adjusted to pH 3.5 or 4.0 with phosphoric acid or sodium hydroxide and then heated with a continuous direct heat sterilization apparatus at 120° C. for 15 seconds. This was spray-dried to obtain a soybean protein powder.

Example 5

Preparation: Phytase (Defatted Soybean Milk)

The defatted soybean milk prepared in Example 1 was adjusted to pH 3.0 with phosphoric acid and warmed to 40° C. To this solution (phytic acid content: 2.20% by weight; TAC solubilization degree: 8.6%) was added the phytase as described in Example 1 in an amount corresponding to 8 units relative to the solid content and the enzymatic reaction was carried out for 30 minutes. After completion of the reaction, the reaction mixture (phytic acid content: 0.05% by weight/ solid content; TCA solubilization degree: 8.8%) treated with the enzyme was heated at pH 3.0 with a continuous direct heat sterilization apparatus at 120° C. for 15 seconds. This solution was adjusted to pH 5.0 with sodium hydroxide and centrifuged at 2,000 G with a centrifugal separator (decanter) to obtain an insoluble fraction (acid precipitated curd) and a soluble fraction (whey). Water was added to the acid precipitated curd so that the solid content was 10% by weight to obtain an acid precipitated curd slurry. This acid precipitated slurry was adjusted to pH 3.0 with an organic acid mixture (citric acid:malic acid=2:3) and then heated with a continuous direct heat sterilization apparatus at 120° C. for 15 seconds. This was spray-dried to obtain a soybean protein powder.

A solution was prepared by dispersing each of the powders obtained in Examples 1 to 5 and Comparative Example 1 so that the protein content was 5% by weight and thoroughly stirring. The solution was adjusted to pH 3.5, 4.0 or 4.5 with a diluted alkaline solution or a diluted acid solution. Then, the solution was subjected to solubility and transmittance determination and a storage test. The storage test was carried out by sterilizing the solution by heating up to 95° C. and storing in a refrigerator for 30 days to observe precipitation with the naked eye. The results are shown in Table 1.

TABLE 1

| Test No. | Before treatment | Heat treatment pH | pH of solution | Solubility % | Transmittance % T | Storage test presence of ppt. |
|---|---|---|---|---|---|---|
| Comp. Ex. 1 | | 3.0 | 3.5 | 93 | 6.4 | ± |
| | | | 4.0 | 64 | 0.1 | + |
| | | | 4.5 | 3 | <0.1 | ++ |
| | | 3.5 | 3.5 | 78 | 0.5 | + |
| | | | 4.0 | 61 | 0.1 | + |
| | | | 4.5 | 5 | <0.1 | ++ |
| Ex. 1 | Phytase | 3.0 | 3.5 | 99 | 83.3 | − |
| | | | 4.0 | 98 | 82.8 | − |
| | | | 4.5 | 95 | 60.7 | − |
| | Phytase | 3.5 | 3.5 | 98 | 67.7 | − |
| | | | 4.0 | 98 | 67.5 | − |
| | | | 4.5 | 94 | 41.6 | − |

TABLE 1-continued

| Test No. | Before treatment | Heat treatment pH | pH of solution | Solubility % | Transmittance % T | Storage test presence of ppt. |
|---|---|---|---|---|---|---|
| | Phytase | 4.0 | 3.5 | 95 | 31.8 | − |
| | | | 4.0 | 95 | 31.5 | − |
| | | | 4.5 | 93 | 23.6 | − |
| Ex. 2 | Chitosan | 3.5 | 3.5 | 99 | 69.7 | − |
| | | | 4.0 | 98 | 68.8 | − |
| | | | 4.5 | 95 | 62.1 | − |
| Ex. 3 | Ca | 3.5 | 3.5 | 96 | 67.3 | − |
| | | | 4.0 | 94 | 63.6 | − |
| | | | 4.5 | 91 | 25.0 | − |
| Ex. 4 | Phytase + Chitosan | 3.5 | 3.5 | 99 | 85.6 | − |
| | | | 4.0 | 99 | 85.6 | − |
| | | | 4.5 | 97 | 80.3 | − |
| | Phytase + Chitosan | 4.0 | 3.5 | 96 | 61.1 | − |
| | | | 4.0 | 95 | 60.9 | − |
| | | | 4.5 | 95 | 58.5 | − |
| Ex. 5 | Phytase | 3.5 | 3.5 | 98 | 86.5 | − |
| | | | 4.0 | 98 | 86.4 | − |
| | | | 4.5 | 97 | 70.1 | − |

(Definition of Symbols) Presence of Precipitate
−: no precipitate, ±: slight precipitation,
+: presence of precipitate, ++: remarkable precipitate In case of Comparative Example 1, when pH of the heat treatment was lowered, the solubility tended to be improved at pH 3.5. However, precipitation assumed to be isoelectric precipitation occurred at pH 4.0 or higher regardless of pH of the heat treatment. Further, even when the heat treatment was carried out at pH 3.0 and the solution was pH 3.5, a cloudy solution having a low transmittance was resulted and precipitation during storage was hardly suppressed. In view of these results, a soybean protein having excellent solubility and transparency at pH 3.5 to 4.5 and excellent storage stability could not be obtained only by the heat treatment at above 100° C.

In contrast, in case of Examples 1 to 3, the products had the solubility of 90% or more and the transmittance of 20% T or more with no precipitation during storage, and the product having the desired quality were obtained regardless of pH of the heat treatment. Nevertheless, although the product having the desired quality was obtained by the heat treatment at pH 4.0, the transmittance somewhat became lower in comparison with the heat treatment at the lower pH. Then, as shown by the product of Example 4, by addition of chitosan before heating, the protein having the high transmittance could be obtained, even when pH of the heat treatment was raised to 4.0, and a synergistic effect was recognized.

Example 6

Hydrolysate: Phytase/Chitosan

The acid precipitated curd slurry having a solid content of 10% by weight prepared in Example 1 was adjusted to pH 3.5 with phosphoric acid and then warmed to 50° C. To this solution was added a protease derived from a microorganism ("Sumityme AP" manufactured by Shin Nippon Kagaku Kogyo) in an amount of 1% relative to the solid content, and hydrolysis was carried out for 1 hour. After the completion of the reaction, the hydrolysate (TCA solubilization degree: 45.5%) was adjusted to pH 3.5 and divided into three portions. The temperature of the first portion was lowered to 40° C., to this was added the phytase as described in Example 1 in an amount corresponding to 8 units relative to the solid content and the enzymatic reaction was carried out for 30 minutes at pH 3.5. After completion of the reaction, the reaction mixture thus treated with the enzyme (phytic acid content: 0.04% by weight/solid content; TCA solubilization degree: no substantial change) was adjusted to pH 3.5 and was heated with a continuous direct heat sterilization apparatus at 120° C. for 15 seconds. To the second portion was added chitosan as described in Example 2 in an amount of 5.0% by weight based on the solid content. After thoroughly stirring, pH was adjusted to 3.5 and the mixture was heated with a continuous direct heat sterilization apparatus at 120° C. for 15 seconds. The third portion was subjected to combination of the phytase treatment and addition of chitosan (1.0% by weight based on the solid content). The mixture was adjusted to pH 3.5 and heated with a continuous direct heat sterilization apparatus at 120° C. for 15 seconds. These were spray-dried to obtain soybean protein powders.

Comparative Example 2

Hydrolysate

The hydrolysate with the protease prepared in Example 6 was adjusted to pH 3.5 and heated with a continuous direct heat sterilization apparatus at 120° C. for 15 seconds. This was spray-dried to obtain a powder of the hydrolysate.

Each of the powders obtained in Example 6 and Comparative Example 2 was dispersed so that the protein content was 5% by weight and thoroughly stirred to obtain a solution. The solution was adjusted to pH 3.5, 4.0 or 4.5 with a diluted alkaline solution. Then, the solution was subjected to solubility and transmittance determination and a storage test. The storage test was carried out by sterilizing the solution by heating up to 95° C. and storing in a refrigerator for 30 days to observe precipitation with the naked eye. The results are shown in Table 2.

In case of Comparative Example 2, precipitation assumed to be isoelectric precipitation occurred at pH 4.0 or higher. Further, even when the solution was pH 3.5, it was a cloudy solution having a low transmittance and precipitation during storage was hardly suppressed. In view of these results, similarly to Comparative Example 1, excellent solubility and transparency at pH 3.5 to pH 4.5 and excellent storage stability could not be provided to a hydrolysate only by the heat treatment at above 100° C., either.

In contrast, in case of Example 6, the product had the solubility of 90% or more and the transmittance of 20% T or more with no precipitation during storage at pH 3.5 and 4.0 by the treatment with the phytase or addition of chitosan, while precipitation assumed to be isoelectric precipitation occurred at pH 4.5. Thus, the product having excellent solubility and transparency and excellent storage stability was obtained at pH 4.0 or lower. Further, as shown by the product of Example 4, the protein having the high transmittance could be obtained by combination of the treatment with the phytase and addition of chitosan and a synergistic effect was recognized.

Example 7

Commercially Available SPI

A commercially available SPI ("New Fujipro R" manufactured by Fuji Oil Co., Ltd.; protein content: 90%) was dispersed in water so that the solid content became 8% and the dispersion was thoroughly stirred, adjusted to pH 3.5 with phosphoric acid, and warmed to 40° C. The resultant solution (phytic acid content: 2.2% by weight/solid content; TCA solubilization degree: 5.0%) was divided into two portions. To one of the two portions was added the phytase as described in Example 1 in an amount corresponding to 8 units relative to the solid content and the enzymatic reaction was carried out for 30 minutes. After completion of the reaction, the reaction mixture thus treated with the enzyme (phytic acid content: 0.03% by weight/solid content; TCA solubilization degree: 5.1% change) was heated with a continuous direct heat sterilization apparatus at 140° C. for 15 seconds. To the other portion was added chitosan as described in Example 2 in an amount of 5.0% by weight based on the solid content. After thoroughly stirring, pH was adjusted to 3.5 and the mixture was heated with a continuous direct heat sterilization apparatus at 140° C. for 15 seconds. These were spray-dried to obtain soybean protein powders.

Comparative Example 3

Commercially Available SPI

The same commercially available soybean protein isolate as that of Example 7 was dispersed in water so that the solid content was 8%. After thoroughly stirred, the dispersion was adjusted to pH 3.5 with phosphoric acid. This was heated with a continuous direct heat sterilization apparatus at 140° C. for 15 seconds. This was spray-dried to obtain a soybean protein powder.

Each of the powders obtained in Example 7 and Comparative Example 3 was dispersed so that the protein content was 5% by weight and thoroughly stirred to obtain a solution. The solution was adjusted to pH 3.5, 4.0 or 4.5 with a diluted alkaline solution. Then, the solution was subjected to solubility and transmittance determination and a storage test. The storage test was carried out by sterilizing the solution by heating up to 95° C. and storing in a refrigerator for 30 days to observe precipitation with the naked eye. The results are shown in Table 2.

In case of Comparative Example 3, solubility was still 80% or lower and precipitation could not be suppressed. In contrast, in case of Example 7, the product having such excellent solubility as 90% or more together with transparency and free from precipitation during storage at pH 3.5 and 4.0 could be obtained even from the commercially available soybean protein isolate by the treatment with the phytase or addition of chitosan.

TABLE 2

| Test No. | Before treatment | Heat treatment pH | pH of solution | Solubility % | Transmittance % T | Storage test presence of ppt. |
|---|---|---|---|---|---|---|
| Comp. Ex. 2 | | 3.5 | 3.5 | 70 | 0.2 | + |
| | | | 4.0 | 50 | <0.1 | ++ |
| | | | 4.5 | 48 | <0.1 | ++ |
| Ex. 6 | Phytase | 3.5 | 3.5 | 95 | 60.5 | − |
| | | | 4.0 | 92 | 56.2 | − |
| | | | 4.5 | 65 | 10.1 | + |
| | Chitosan | 3.5 | 3.5 | 96 | 61.3 | − |
| | | | 4.0 | 92 | 57.2 | − |
| | | | 4.5 | 60 | 11.8 | + |
| | Phytase + Chitosan | 3.5 | 3.5 | 98 | 85.9 | − |
| | | | 4.0 | 95 | 80.2 | − |
| | | | 4.5 | 68 | 16.0 | + |

TABLE 2-continued

| Test No. | Before treatment | Heat treatment pH | pH of solution | Solubility % | Transmittance % T | Storage test presence of ppt. |
|---|---|---|---|---|---|---|
| Com. Ex. 3 | | 3.5 | 3.5 | 76 | <0.1 | + |
| | | | 4.0 | 60 | <0.1 | + |
| | | | 4.5 | 15 | <0.1 | + + |
| Ex. 7 | Phytase | 3.5 | 3.5 | 98 | 38.4 | − |
| | | | 4.0 | 97 | 37.7 | − |
| | | | 4.5 | 95 | 30.1 | − |
| | Chitosan | 3.5 | 3.5 | 96 | 36.7 | − |
| | | | 4.0 | 96 | 36.0 | − |
| | | | 4.5 | 94 | 31.2 | − |

Example 8

Commercially Available Soybean Milk

Commercially available soybean milk ("Soybean Milk Plane" manufactured by Toraku; solid content: 7% or higher, protein content: 3.8%; lipid content: 3.2%) was adjusted to pH 3.5 with phosphoric acid and then warmed to 40° C. This solution (phytic acid content: 2.1% by weight/solid content; TCA solubilization degree: 8.8%) was divided into two portions. To one of the two portions was added the phytase as described in Example 1 in an amount corresponding to 8 units relative to the solid content and the enzymatic reaction was carried out for 30 minutes. After completion of the reaction, the reaction mixture thus treated with the enzyme (phytic acid content: 0.04% by weight/solid content; TCA solubilization degree: 9.0%) was heated with a continuous direct heat sterilization apparatus at 120° C. for 15 seconds. To the other portion was added chitosan as described in Example 2 in an amount of 5.0% by weight based on the solid content. After thoroughly stirring, pH was adjusted to 3.5 and the mixture was heated with a continuous direct heat sterilization apparatus at 120° C. for 15 seconds.

Comparative Example 4

Commercially Available Soybean Milk

The same commercially available soybean milk as that of Example 8 was adjusted to pH 3.5 and heated with a continuous direct heat sterilization apparatus at 120° C. for 15 seconds.

Each of the soybean milk obtained in Example 8 and Comparative Example 4 was adjusted to pH 3.5, 4.0 or 4.5 with a diluted alkaline solution. Then, the solution was subjected to determination of a precipitation degree and a storage test. The storage test was carried out by sterilizing the solution by heating up to 95° C. and storing in a refrigerator for 30 days to observe precipitation with the naked eye. The results are shown in Table 3. The precipitation degree was calculated in terms of a ratio of precipitated solids (formed by centrifuging a solution, which was prepared by dispersing a sample so that the solid content was 7% by weight and thoroughly stirring, at 10,000 G for 5 minutes, if necessary after adjusting pH), to the total solid content.

In case of Comparative Example 4, remarkable aggregation and precipitation were observed at pH 4 or higher and the precipitation degree was more than 10% even at pH 3.5. This showed an unstable state. In contrast, in case of Example 8, although precipitation assumed to be isoelectric precipitation occurred at pH 4.5, the product had the precipitation degree of 10% or less with no precipitation during storage at pH 3.5 and 4.0. This showed high stability.

TABLE 3

| Test No. | Before treatment | Heat treatment pH | pH of solution | Precipitation degree % | Storage test presence of ppt. |
|---|---|---|---|---|---|
| Comp. Ex. 4 | | | 3.5 | 18 | ± |
| | | | 4.0 | 80 | + + |
| | | | 4.5 | 82 | + + |
| Ex. 8 | Phytase | 3.5 | 3.5 | 7 | − |
| | | | 4.0 | 7 | − |
| | | | 4.5 | 78 | + + |
| | Chitosan | 3.5 | 3.5 | 7 | − |
| | | | 4.0 | 8 | − |
| | | | 4.5 | 80 | + + |

Comparative Example 5

Comparison of Heating Temperature

Each of the product prepared by treating with the phytase in Example 1, the product prepared by treating the hydrolysate with the phytase in Example 6, and the product prepared by treating the commercially available soybean protein isolate with the phytase in Example 7 was subjected to a heat treatment at pH 3.5 and at 98° C. for 10 minutes by batch process and spray-dried to obtain a soybean protein powder.

Each of the powders obtained in Comparative Example 5 was dispersed so that the protein content was 5% by weight and thoroughly stirred to prepare a solution. The solution was adjusted to pH 4.0 with a diluted alkaline solution and subjected to the determination of solubility and transmittance and storage test. As shown in Table 4, in all the samples, the desired quality level can not be achieved by the heat treatment at up to 100° C.

TABLE 4

| Test No. | Sample | Heating temp. °C. | pH of solution | Solubility % | Transmittance % T | Storage test presence of ppt. |
|---|---|---|---|---|---|---|
| Comp. Ex. 5 | Ex. 1 | 98 | 3.5 | 75 | 0.1 | + |
| | Ex. 2 | 98 | 3.5 | 87 | 10.8 | ± |
| | Ex. 3 | 98 | 3.5 | 70 | <0.1 | + + |

Example 9

Emulsifying Activity and Load at Gel Break

An evaluation of functionality (emulsifying capability and gel-forming capability) of the soybean protein obtained in the present invention was carried out. The emulsifying capability was evaluated by determining an emulsifying activity. The results are shown in Table 5. The emulsifying activity was determined as followed. Each of the powders obtained by the heat treatment at pH 3.5 in Examples 1 and 2 and by the heat treatment at pH 3.0 in Comparative Example 1 was dispersed so that the solid content was 1% by weight and thoroughly stirred to prepare a solution. The solution was adjusted to pH 3.5, 4.0 or 4.5 with a diluted alkaline solution and to 3 ml of the solution was added 1 ml of soybean oil. The mixture was treated with a ultrasonic dispersing device to prepare an emulsion. A 1,000-fold dilution of the emulsion was prepared with a 0.1% by weight SDS solution and turbidity of the dilution (absorbance at 500 nm) was determined. In this evaluation, a higher turbidity was judged to be a higher emulsifying activity. According to this method, the emulsifying activities of the powders obtained in Examples 1 and 2 and Comparative Example 1 were determined. Although the powder of Comparative Example 1 showed a slight emulsifying activity at pH 3.5, the powders of Examples 1 and 2 showed high emulsifying activities regardless of pH.

The gel-forming capability was evaluated by determining jelly strength. The jelly strength was determined as follows. A paste containing 18% by weight of each of the powders obtained by the heat treatment at pH 3.5 in Examples 1 and 2 and by the heat treatment at pH 3.0 in Comparative Example 1 was prepared (4.5-fold water was added to the powder) and adjusted to pH 3.5, 4.0 or 4.5 with a diluted alkaline solution. The paste was filled into a casing of 35 mm folding diameter and heated at 80° C. After cooling, the jelly strength was determined by a rheometer (manufactured by Sanden-sha) with a plunger ball of 5 mm diameter. Although the powder of Comparative Example 1 showed a slight load at gel break at pH 3.5, the powders of Examples 1 and 2 showed high load at gel break regardless of pH.

These results clearly showed the superiority in both emulsifying capability and gel-forming capability of the products of Examples 1 and 2.

TABLE 5

| Test No | Heat treatment pH | pH of solution | Emulsifying activity OD 500 nm | Load at gel break gf/ |
|---|---|---|---|---|
| Comp. Ex. 1 | 3.0 | 3.5 | 0.24 | 155 |
|  |  | 4.0 | 0.03 | 54 |
|  |  | 4.5 | 0.02 | no gelation |
| Example 1 | 3.5 | 3.5 | 0.67 | 468 |
|  |  | 4.0 | 0.60 | 440 |
|  |  | 4.5 | 0.50 | 403 |
| Example 2 | 3.5 | 3.5 | 0.70 | 502 |
|  |  | 4.0 | 0.69 | 455 |
|  |  | 4.5 | 0.65 | 438 |

Example 10

Application Example in Beverage

According to the formulation of the powder obtained in Example 1 (heating pH: 3.5, 8.0 parts), liquid fructose-glucose (manufactured by Nippon Corn Starch, 8.0 parts), 5-fold concentrated apple juice (manufactured by Food Material, 2.0 parts), apple flavor (manufactured by Takasago Koryo, 0.2 part) and water (81.8 parts), an acid soybean protein beverage was experimentally prepared by thoroughly mixing the ingredients with stirring, adjusting pH to 3.8 with sodium citrate, and then sterilizing the mixture by heating up to 95° C. The beverage thus obtained had high transparency and high storage stability. Further, since no stabilizer and emulsifier were used, viscosity was low and the beverage was easy to drink.

Example 11

Application Example in Jelly Beverage

According to the formulation of the powder obtained in Example 7 (combination of the phytase treatment and chitosan treatment, 5.0 parts), liquid fructose-glucose (manufactured by Nippon Corn Starch, 8.0 parts), 5-fold concentrated pineapple juice (manufactured by Food Material, 2.5 parts), agar (manufactured by Ina Kanten, 0.3 part), pineapple flavor (manufacture by Takasago Koryo, 0.2 part) and water (84.0 parts), a soybean protein jelly beverage was experimentally prepared by thoroughly mixing the ingredients other than agar with stirring, adjusting pH to 3.6 with sodium citrate, sterilizing the mixture by heating up to 95° C., mixing the resultant with a solution of the agar, which had been swollen by heating, while the solution being hot, filling the mixture in a cheer pack and gelling the mixture in a refrigerator overnight. The jelly beverage obtained had the desired transparency and good mouthfeel. Further, changes such as turbidity and precipitation were not caused during storage.

INDUSTRIAL APPLICABILITY

The soybean protein obtained by the process of the present invention has improved solubility in an acidic region. Thus, the protein can be used as a protein material for foods in an acidic region where a conventional material can not be used because such a material causes precipitation and aggregation. Further, a protein material which provides a solution having not only high solubility but also high transparency can be obtained by using a defatted raw material. Thus, it is possible to provide acidic foods free from cloudy. The protein material can be suitably used as a material for functional foods having gelling and emulsifying properties under acidic conditions, which makes it possible to broaden the category of acidic foods and variety of protein ingestion in eating habits.

The invention claimed is:

1. A process for producing a soybean protein material characterized in that a solution containing a soybean protein is subjected to (A) a treatment for eliminating or inactivating polyanionic substances which are derived from the protein source and contained in the solution, or (A) and (B) a treatment for adding a polycationic substance to the solution; and then the protein solution is adjusted to pH 2.3 to 4.3 without carrying out an operation for removing insoluble matter, and subjected to a heat treatment at a temperature above 100° C. at that pH.

2. The process for producing a soybean protein material according to claim 1, wherein the treatment for eliminating or inactivating polyanionic substances is carried out by eliminating or inactivating phytic acid.

3. The process for producing a soybean protein material according to claim 2, wherein the treatment for eliminating or inactivating phytic acid is carried out by either or both of a treatment with a phytase, and addition of a polyvalent metal ion of divalent or higher.

4. A process for producing a soybean protein hydrolysate characterized in that a solution containing a soybean protein is subjected to (A) a treatment for eliminating or inactivating polyanionic substances which are derived from the protein source and contained in the solution, or (A) and (B) a treatment for adding a polycationic substance to the solution, and to a hydrolyzation treatment of the protein with a protease; and then the protein solution is adjusted to pH 2.3 to 4.3 without carrying out an operation for removing insoluble mater, and subjected to a heat treatment at a temperature above 100° C. at that pH.

5. The process for producing a soybean protein material according to claim 1, wherein the heated product is dried at pH 4.5 or below.

6. The process for producing a soybean protein material according to claim 1, wherein the solution containing a soybean protein is soybean milk.

7. The process for producing a soybean protein hydrolysate according to claim 4, wherein the heated product is dried at pH 4.5 or below.

8. The process for producing a soybean protein hydrolysate according to claim 4, wherein the solution containing a soybean protein is soybean milk.

* * * * *

UNITED STATES PATENT AND TRADEMARK OFFICE
CERTIFICATE OF CORRECTION

| | | |
|---|---|---|
| PATENT NO. | : 7,465,470 B2 | Page 1 of 1 |
| APPLICATION NO. | : 10/469348 | |
| DATED | : December 16, 2008 | |
| INVENTOR(S) | : Tsutomu Saito et al. | |

It is certified that error appears in the above-identified patent and that said Letters Patent is hereby corrected as shown below:

On the title page

Item (75), first inventor, "Tsutomo" should read --Tsutomu--.

Signed and Sealed this
Twentieth Day of March, 2012

David J. Kappos
*Director of the United States Patent and Trademark Office*